(12) United States Patent
Helfteren

(10) Patent No.: US 8,449,581 B2
(45) Date of Patent: May 28, 2013

(54) SLIDING PLATE WITH REINFORCED SLOT

(75) Inventor: Alwin Van Helfteren, Freiburg (DE)

(73) Assignee: Stryker Trauma GmbH (DE)

( * ) Notice: Subject to any disclaimer, the term of this patent is extended or adjusted under 35 U.S.C. 154(b) by 1273 days.

(21) Appl. No.: 11/800,662

(22) Filed: May 7, 2007

(65) Prior Publication Data

US 2008/0281327 A1 Nov. 13, 2008

(51) Int. Cl.
*A61B 17/80* (2006.01)
*A61B 17/58* (2006.01)

(52) U.S. Cl.
USPC .............................. 606/280; 606/283; 606/908

(58) Field of Classification Search
USPC .............. 606/70–71, 101, 280–299, 902–906
See application file for complete search history.

(56) References Cited

U.S. PATENT DOCUMENTS

| | | | |
|---|---|---|---|
| 4,573,458 A | 3/1986 | Lower | |
| 4,800,874 A * | 1/1989 | David et al. | 606/286 |
| 5,087,259 A | 2/1992 | Krenkel et al. | |
| 5,372,598 A | 12/1994 | Luhr et al. | |
| 5,681,311 A * | 10/1997 | Foley et al. | 606/283 |
| 5,785,712 A | 7/1998 | Runciman et al. | |
| 5,868,746 A | 2/1999 | Sarver et al. | |
| 5,961,519 A * | 10/1999 | Bruce et al. | 606/280 |
| 6,096,040 A | 8/2000 | Esser | |
| 6,221,075 B1 | 4/2001 | Tormala et al. | |
| 6,283,969 B1 * | 9/2001 | Grusin et al. | 606/280 |
| 6,325,803 B1 | 12/2001 | Schumacher et al. | |
| 6,423,068 B1 | 7/2002 | Reisberg et al. | |
| 6,755,832 B2 | 6/2004 | Happonen et al. | |
| 6,960,211 B1 * | 11/2005 | Pfefferle et al. | 606/282 |
| 7,220,263 B2 * | 5/2007 | Cordaro | 606/70 |
| 7,341,590 B2 * | 3/2008 | Ferree | 606/915 |
| 7,491,220 B2 * | 2/2009 | Coughln | 606/280 |
| 7,537,604 B2 * | 5/2009 | Huebner | 606/281 |
| 2002/0128653 A1 | 9/2002 | Haidukewych | |
| 2003/0060827 A1 * | 3/2003 | Coughln | 606/70 |

(Continued)

FOREIGN PATENT DOCUMENTS

| DE | 10125092 | 12/2001 |
|---|---|---|
| DE | 202005019277 U | 2/2006 |

(Continued)

OTHER PUBLICATIONS

Tekka—Createur d'implants L'entreprise, Maxillofacial Orthognatic Surgery Site Adjustable Plates, website printout (www.tekka.fr), Apr. 19, 2007.

(Continued)

*Primary Examiner* — Kevin T Truong
*Assistant Examiner* — Larry E Waggle, Jr.
(74) *Attorney, Agent, or Firm* — Lerner, David, Littenberg, Krumholz & Mentlik, LLP

(57) ABSTRACT

A bone plate that may be used to maintain relative position of two pieces of fractured bone, for example, a fractured jaw bone. The bone plate has a slot and holes. The holes are surrounded by walls and the slot is also surrounded by walls. The thickness of walls surrounding the slot at their maximum is greater than the thickness of walls surrounding the holes. Often the nature of the fracture may require bending of the plate for implanting it as desired by the surgeon. Because walls of the slot are designed to be strong, the slot is not deformed when the plate is bent.

15 Claims, 4 Drawing Sheets

U.S. PATENT DOCUMENTS

| | | |
|---|---|---|
| 2004/0116930 A1 * | 6/2004 | O'Driscoll et al. ............. 606/69 |
| 2005/0182408 A1 | 8/2005 | Pfefferle et al. |
| 2006/0173459 A1 * | 8/2006 | Kay et al. ........................ 606/69 |
| 2006/0200145 A1 | 9/2006 | Kay et al. |
| 2007/0162013 A1 * | 7/2007 | Jacene et al. .................... 606/69 |

FOREIGN PATENT DOCUMENTS

| | | |
|---|---|---|
| EP | 1468656 | 10/2004 |
| EP | 1468656 A1 * | 10/2004 |
| FR | 2785519 A1 * | 5/2000 |
| FR | 2862862 A1 * | 6/2005 |
| WO | WO 2005023127 A1 * | 3/2005 |

OTHER PUBLICATIONS

Jallut, Gleitloch-Miniplatten Gliding Hole Miniplate, Mondeal Medical Systems GMBH Germany, 1999.

* cited by examiner

400
SLIDING PLATE WITH REINFORCED SLOT

BACKGROUND OF THE INVENTION

The present invention relates to a bone plate, in particular, a bone plate for maintaining relative position of two pieces of fractured jaw bone.

Bone plates are widely used to maintain fractured bones in a fixed relative position. FIG. 3 shows a conventional bone plate 100. Conventional bone plate 100 has a slot 102 and holes 104. Holes 104 are surrounded by walls 106 and slot 102 is surrounded by walls 108. The diameter of holes 104 and the width of slot 102 are same. Since the maximum width of the bone plate measured at holes 104 and slot 102 are equal, the thickness of walls 106 and 108 are same. Often the nature and location of the fractures, and the bone contour at the fracture site, may require bending of plate 100 for implanting it as desired by the surgeon. Plate 100 may be bent side to side in the plane of plate 100 and additionally may also be bent transverse to the plane of plate 100. In conventional plates 100, when the plate is bent, as shown in FIG. 4, slot 102 can deform. Often when slot 102 deforms, the opening of slot 102 is, at portions, larger than at other portions and often larger than the head of the fastener used in slot 102. Therefore, there is a need for an improved bone plate wherein the slot would not get deformed when it is necessary to bend the plate.

SUMMARY OF THE INVENTION

The present invention provides a bone plate that may be used to maintain relative position of two pieces of fractured bone, for example, a fractured jaw bone. The bone plate of present invention has a slot and holes. The holes are surrounded by walls and the slot is also surrounded by walls. The thickness of walls surrounding the slot at their maximum is greater than the thickness of walls surrounding the holes.

In use, the bone plate is first attached to a first fragment of fractured bone. Next, bone fragments are aligned and the other end of the bone plate is attached to second fragment. Since the attachment to the second fragment is via a screw inserted in the slot, the first fragment and the second fragment can be moved relative to each other. Once the first fragment and the second fragment are brought in relative positions desired by the surgeon, additional screw are inserted into second fragment and first fragment. Often the nature of the fracture may require bending of the plate for implanting it as desired by the surgeon. The plate of present invention has an elongated neck portion where the plate may be bent. Because walls of the slot are designed to be strong, the slot is not deformed when the plate is bent.

DETAILED DESCRIPTION

Figure 1:
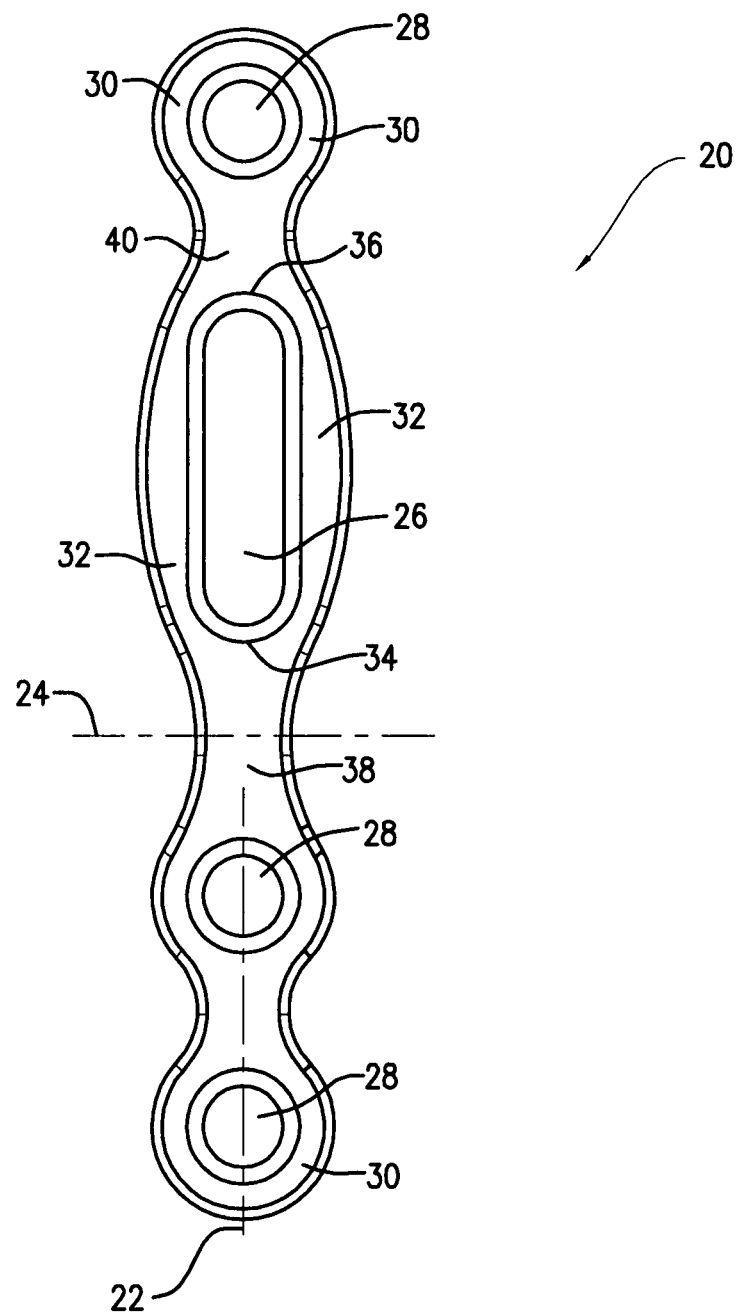
FIG. 1 shows a plan view of an embodiment of a bone plate of present invention.

FIG. 1 shows a bone plate 20. Bone plate 20 may be used to maintain relative position of two pieces of fractured bone, for example, a fractured jaw bone. Bone plate 20 is an elongate part made from bio-compatible material. Bone plate 20 has a longitudinal axis 22 and a transverse axis 24. Bone plate 20 has a slot 26 and holes 28. Holes 28 may be located on one side or both side of slot 26. Bone plate 20 may have one or more holes 28. The Holes 28 are surrounded by walls 30 and slot 26 is surrounded by walls 32. The outer contour of plate 20 around holes 28 may be circular and the outer contour of plate 20 around slot 28 may be arcuate. The outer contours of the plate may take other shapes. In the embodiment of FIG. 1 having the outer contour around holes 28 circular and the outer contour around slot 26 arcuate, the thickness of the walls 30 are measured radially from the centre of the corresponding holes 28 and the thickness of the walls 32 are measured parallel to transverse axis 24. The thicknesses of walls 30 are constant whereas the thicknesses of the walls 32 vary at different points along the length of slot 26 though in a preferred embodiment it is not necessary that the walls 32 be different in thickness at every point. In a preferred embodiment, the max thickness is at the central region of the slot 26. The thickness of walls 32 at their maximum is greater than the thickness of walls 30. In another embodiment, wall 32 may have a constant thickness that is greater than walls 30. Slot 26 has a first end 34 and a second end 36. A hole 28 that is located near the first end 34 is connected to the first end 34 via a neck 38. A hole 28 that is located near the second end 36 is connected to the second end 34 via a neck 40. The width of bone plate 20 is measured parallel to the transverse axis 24 and is narrower in the neck area.

Figure 2:
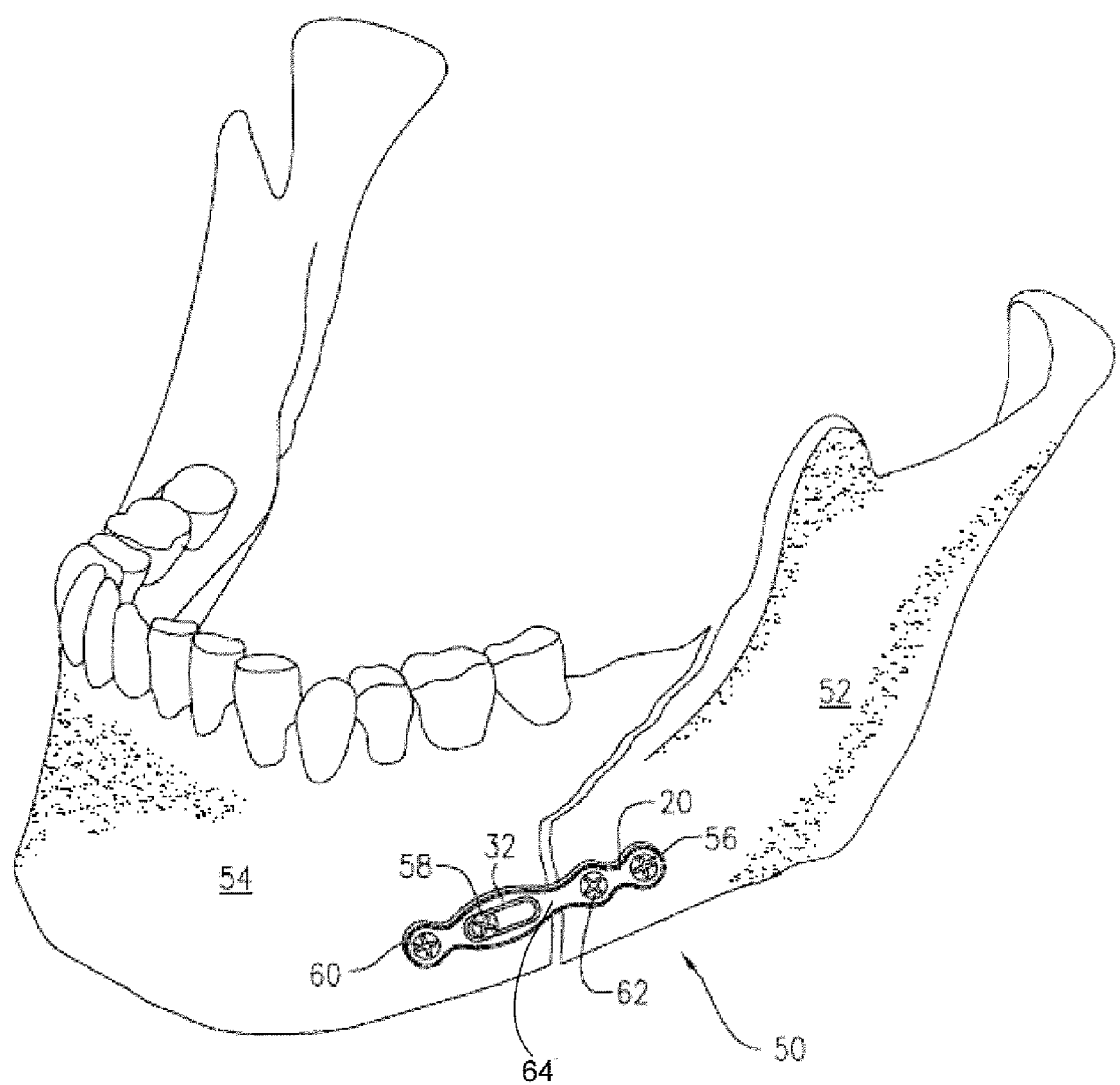
FIG. 2 shows a pictorial view of a bone plate implanted on a jaw bone.
Figure 3:
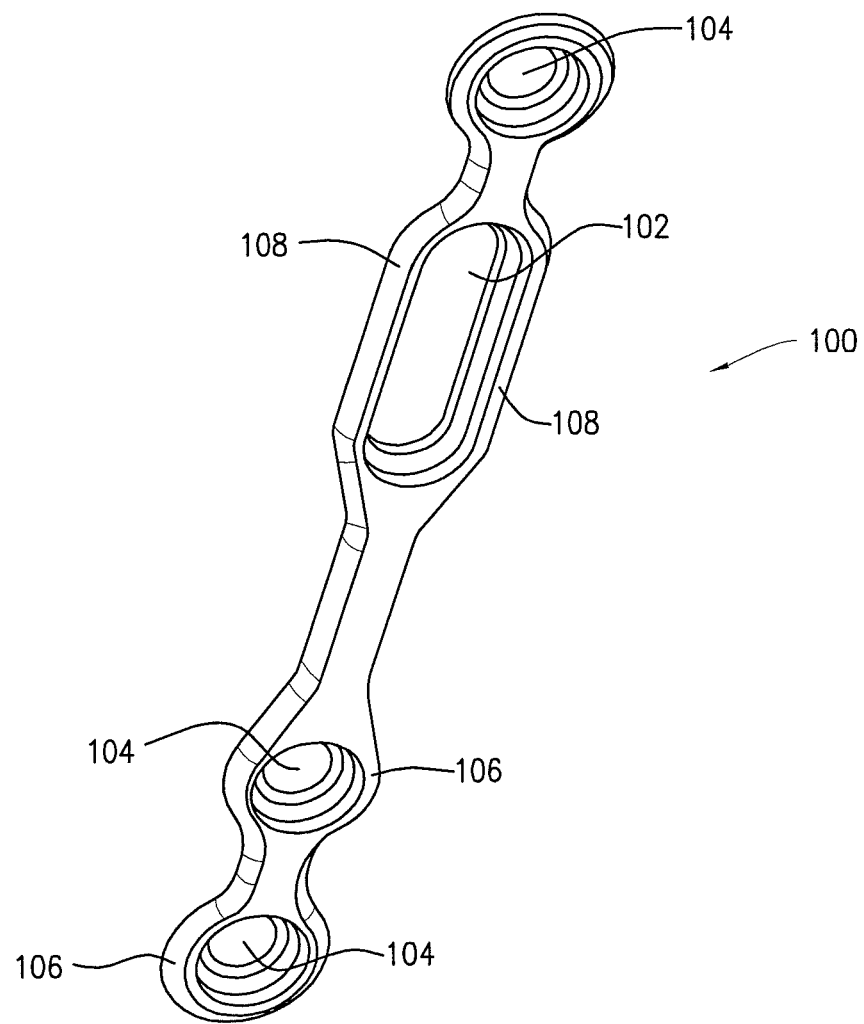
FIG. 3 shows a conventional bone plate.
Figure 4:
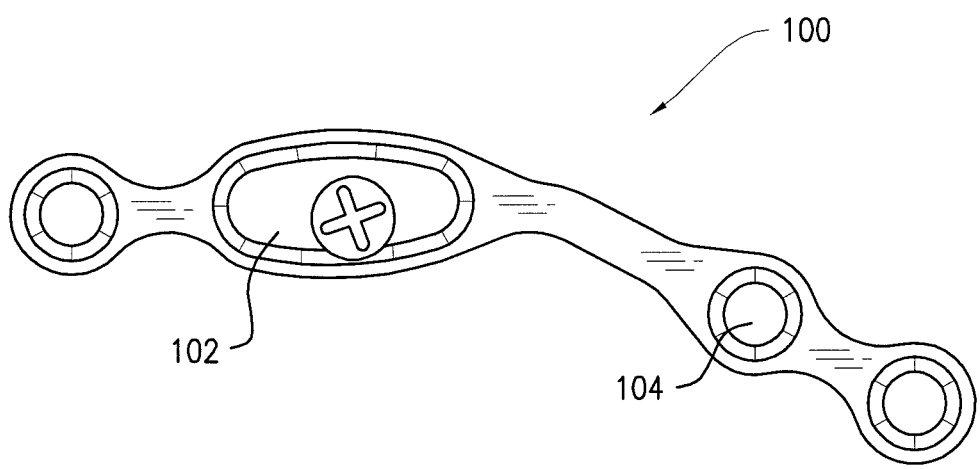
FIG. 4 shows a conventional plate that has been bent.

FIG. 2 shows a bone plate 20 attached to first fragment 52 and second fragment 54 of a fractured jaw bone 50. In use, bone plate 20 may be first attached to first fragment 52 of fractured bone 50 by placing one hole 28 of bone plate 20 on the first fragment 52 and inserting a screw 56 through hole 28 and into bone 50. Next, bone fragments 52 and 54 may be aligned and the other end of bone plate 20 may be attached to second fragment 54 by inserting screw 58 through slot 26 and in second fragment 54 of bone 50. Since screw 58 is inserted in a slot, it gives the surgeon flexibility to reduce the fracture, i.e., align first fragment 52 and the second fragment 54 after screw 58 is inserted. Once first fragment 52 and the second fragment 54 are brought in relative positions desired by the surgeon, additional screw 60 and thereafter screw 62 are inserted via respective holes 28 into second fragment 54 and first fragment 52 respectively. Often the nature and location of the fracture, and the contour of the bone site, may require bending of plate 20 for implanting it as desired by the surgeon. Plate 20 has an elongated neck portion 64 where the plate may be bent. Plate 20 may be bent in the plane of plate 20 or transverse to the plane of plate 20. Plate 20 may also be bent in any other manner deemed necessary by the surgeon. The walls 32 of slot 26 are designed to withstand the bending forces which might be translated to this region as the elongated neck portion 64 is bent. Thus, slot 26 is not deformed when plate 20 is bent intraoperatively to be contoured to the bone at or adjacent a fracture site.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. A bone plate comprising:
an elongate plate;

a slot formed in the elongate plate, the slot having a first wall forming an outer periphery of the slot, wherein a region of the plate defined by the slot has a first plate width;

a first annular hole formed in the plate, the hole having a second wall forming the outer periphery of the hole, wherein a region of the plate defined by the first annular hole has a second plate width; and a neck portion located between the slot and the first annular hole, the neck portion being bendable in the plane of the plate and transverse to the plane of the plate, wherein at least a portion of the first wall is thicker than the second wall, wherein the first wall varies in thickness along the length of the slot and is thickest in the central region of the slot, wherein the first plate width is larger than the second plate width.

2. The bone plate of claim 1, wherein the bone plate is straight and the slot has a first end and a second end, and a second annular hole is formed in the plate, the second hole being located on the first end side of the slot and the first hole being located on the second end side of the slot.

3. The bone plate of claim 2, wherein the distance between the slot and the second hole is less than the distance between the slot and the first hole.

4. The bone plate of claim 2, further comprising;
a second neck portion located between the slot and the second annular hole, the second neck portion being shorter than the neck portion.

5. A bone plate for maintaining relative position of two pieces of fractured bone, the bone plate comprising:
an elongate plate having a longitudinal axis and a transverse axis;
a slot formed in the elongate plate, the length of the slot being parallel to the longitudinal axis of the plate, the width of the slot being parallel to the transverse axis, the slot being surrounded by a slot wall, the slot having a first end and a second end;
a first hole formed in the plate, the first hole being on the first end side of the slot and being surrounded by a first wall;
a first neck portion connecting the first hole to the first end of the slot, the neck portion being bendable in the plane of the plate and transverse to the plane of the plate;
a second hole formed in the plate, the second hole being on the second end side of the slot and being surrounded by a second wall; and
a second neck portion connecting the second hole to the second end of the slot,
wherein the thickness of the slot wall measured in a direction parallel to the transverse axis varies in the longitudinal direction, and a maximum thickness of the slot wall is greater than a maximum thickness of the first wall or the second wall, wherein the slot wall comprises a first side, the first side being straight; and a second side, the second side being generally in the shape of an arc, the first side and the second side having the maximum thickness between them, wherein the slot wall extends past the length of the slot, towards the first and second necks and the plate has a minimum thickness at the first neck.

6. The bone plate of claim 5, wherein the maximum thickness of the slot wall is in the middle of the slot.

7. The bone plate of claim 5, further comprising:
a third hole formed in the plate, the third hole being/located on the first end side of the slot or the second end side of the slot.

8. The bone plate of claim 5, wherein the first neck portion and second neck portion have different lengths.

9. A bone plate comprising;
a plate;
a slot formed in the plate, the slot having a first end and a second end;
a first hole formed in the plate and located on the first end side of the slot;
a second hole formed in the plate and located on the second end side of the slot;
a first neck connecting the first hole to the first end, the plate being bendable at the first neck;
a second neck connecting the second hole to the second end, wherein;
the first neck is longer than the second neck; and
a slot wall around the slot having a varying thickness along the length of the slot, wherein the maximum thickness is located in the middle of the slot, wherein the slot wall extends past the length of the slot towards the first and second necks and the plate has a minimum thickness at the first neck.

10. The bone plate of claim 9, wherein the plate is bendable at the second neck.

11. The bone plate of claim 10, wherein the plate is bendable in the plane of the plate and transverse to the plane of the plate.

12. The bone plate of claim 9, wherein the plate is bendable in the plane of the plate and transverse to the plane of the plate.

13. The bone plate of claim 9, further comprising:
a first wall formed around the first hole;
a second wall formed around the second hole;
wherein at least a portion of the slot wall has a thickness greater then a thickness of the first wall and a thickness of the second wall.

14. A bone plate for reducing a fracture in a bone comprising the bone plate of claim 9, wherein the slot accommodates a bone screw.

15. The bone plate of claim 9, wherein the plate is sized to attach to a jaw bone.

* * * * *

UNITED STATES PATENT AND TRADEMARK OFFICE
CERTIFICATE OF CORRECTION

PATENT NO.        : 8,449,581 B2                                Page 1 of 1
APPLICATION NO.   : 11/800662
DATED             : May 28, 2013
INVENTOR(S)       : Alwin Van Helfteren It is certified that error appears in the above-identified patent and that said Letters Patent is hereby corrected as shown below:

In the Specification
Col. 1, Line 13, after "are" insert --the--.
Col. 1, Line 14, before "equal" "are" should read --is--.
Col. 1, Line 15, after "are" insert --the--.
Col. 1, Line 33, before "present" insert --the--.
Col. 1, Line 39, before "second" insert --a--.
Col. 1, Line 44, "screw" should read --screw s--.
Col. 2, Line 2, "side" should read --sides--.
Col. 2, Line 11, before "measured" delete "are" and insert --is--.
Col. 2, Line 12, before "measured" delete "are" and insert --is--.

In the Claims
Col. 4, Line 46, Claim 13, after "greater" delete "then" and insert --than--.

Signed and Sealed this
Thirty-first Day of March, 2015

Michelle K. Lee
*Director of the United States Patent and Trademark Office*